US011400202B2

(12) United States Patent
Locke et al.

(10) Patent No.: US 11,400,202 B2
(45) Date of Patent: Aug. 2, 2022

(54) SYSTEMS, APPARATUSES, AND METHODS FOR NEGATIVE-PRESSURE TREATMENT WITH PRESSURE DELIVERY INDICATION (71) Applicant: KCI Licensing, Inc., San Antonio, TX (US)

(72) Inventors: Christopher Brian Locke, Bournemouth (GB); Benjamin Andrew Pratt, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 97 days.

(21) Appl. No.: 16/753,478

(22) PCT Filed: Aug. 30, 2018

(86) PCT No.: PCT/US2018/048898
§ 371 (c)(1),
(2) Date: Apr. 3, 2020

(87) PCT Pub. No.: WO2019/089118
PCT Pub. Date: May 9, 2019

(65) Prior Publication Data
US 2020/0289726 A1   Sep. 17, 2020

Related U.S. Application Data (60) Provisional application No. 62/578,933, filed on Oct. 30, 2017.

(51) Int. Cl.
A61M 1/00 (2006.01)
A61F 13/02 (2006.01)
A61F 13/00 (2006.01)

(52) U.S. Cl.
CPC .......... *A61M 1/90* (2021.05); *A61F 13/0216* (2013.01); *A61F 13/0253* (2013.01);
(Continued)

(58) Field of Classification Search
CPC ............ A61M 1/732; A61M 2205/583; A61M 2205/3344; A61M 13/0216;
(Continued)

(56) References Cited

U.S. PATENT DOCUMENTS 1,355,846 A   10/1920  Rannells
2,547,758 A    4/1951  Keeling
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Philip R Wiest
*Assistant Examiner* — Eric Rassavong (57) ABSTRACT A dressing for treating a tissue site with negative pressure may include a core having a first surface, a second surface, and an absorbent between the first surface and the second surface, a cover disposed over the first surface of the core, a pressure indicator configured to change shape under negative pressure, and a fluid conductor coupling the pressure indicator to the second surface of the core.

20 Claims, 8 Drawing Sheets (52) U.S. Cl.
CPC ............... *A61M 1/732* (2021.05); *A61M 1/80* (2021.05); *A61F 2013/00268* (2013.01); *A61F 2013/00702* (2013.01); *A61M 2205/3344* (2013.01); *A61M 2205/583* (2013.01)

(58) Field of Classification Search
CPC ............... A61F 13/0216; A61F 13/0253; A61F 2013/00268; A61F 2013/00702
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0137775 A1* | 6/2010 | Hu .................... A61M 1/732 602/54 |
| 2011/0092927 A1* | 4/2011 | Wilkes ............ A61F 13/00059 604/304 |
| 2014/0114263 A1* | 4/2014 | Weston ................ A61F 15/008 604/318 |
| 2014/0163491 A1 | 6/2014 | Schuessler et al. | |
| 2015/0080788 A1 | 3/2015 | Blott et al. | |
| 2017/0014556 A1* | 1/2017 | Haggstrom ....... A61F 13/00068 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2879633 A1 | 6/2015 |

(56) References Cited

FOREIGN PATENT DOCUMENTS

| | | | | |
|---|---|---|---|---|
| GB | 692578 | A | 6/1953 | |
| GB | 2195255 | A | 4/1988 | |
| GB | 2 197 789 | A | 6/1988 | |
| GB | 2 220 357 | A | 1/1990 | |
| GB | 2 235 877 | A | 3/1991 | |
| GB | 2 329 127 | A | 3/1999 | |
| GB | 2 333 965 | A | 8/1999 | |
| GB | 2511523 | * | 3/2013 | ....... A61F 13/00068 |
| GB | 2511523 | A | 9/2014 | |
| JP | 4129536 | B2 | 8/2008 | |
| SG | 71559 | | 4/2002 | |
| WO | 80/02182 | A1 | 10/1980 | |
| WO | 87/04626 | A1 | 8/1987 | |
| WO | 90/010424 | A1 | 9/1990 | |
| WO | 93/009727 | A1 | 5/1993 | |
| WO | 94/20041 | A1 | 9/1994 | |
| WO | 96/05873 | A1 | 2/1996 | |
| WO | 97/18007 | A1 | 5/1997 | |
| WO | 99/13793 | A1 | 3/1999 | |
| WO | 2012178161 | A1 | 12/2012 | |
| WO | WO-2012178161 | A1 * | 12/2012 | ....... A61F 13/00068 |
| WO | WO-2013114097 | A1 * | 8/2013 | ....... A61F 13/00068 |
| WO | WO-2013136181 | A2 * | 9/2013 | .............. A61M 1/86 |
| WO | WO-2015168681 | A1 * | 11/2015 | .......... A61M 1/0003 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, Nos. May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al.; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al.; "Medical Textiles: Application of an Absorbable Barbed Bi-directional Surgical Suture" Journal of Textile and Apparel, Technology and Management, vol. 2, Issue 2, Spring 2002, pp. 1-5.

Kostyuchenok, B.M., et al.; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al.; "Active Wound Drainage", Vestnki Khirurgi, vol. 138, Issue 4, 1987, and 7 page English translation thereof.

Davydov, Yu.A., et al.; "Bacteriological and Cytological Assessment of Vacuum Therapy for Purulent Wounds" Vestnik Khirugi, Oct. 1988, pp. 48-52, and 8 page English translation thereof.

Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al.; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Bjorn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.L Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion for Corresponding Application No. PCT/US2018/048898, dated Mar. 20, 2019.

* cited by examiner

SYSTEMS, APPARATUSES, AND METHODS FOR NEGATIVE-PRESSURE TREATMENT WITH PRESSURE DELIVERY INDICATION

RELATED APPLICATIONS

This application is a U.S. National Stage Entry of PCT/US2018/048898, filed Aug. 30, 2018, which claims the benefit, under 35 U.S.C. § 119(e), of the filing of U.S. Provisional Patent Application Ser. No. 62/578,933, entitled "Systems, Apparatuses, and Methods for Negative-Pressure Treatment with Pressure Delivery Indication," filed Oct. 30, 2017, which is incorporated herein by reference for all purposes.

TECHNICAL FIELD

The invention set forth in the appended claims relates generally to tissue treatment systems and more particularly, but without limitation, to systems and dressings for negative-pressure treatments, and methods of using systems and dressings for negative-pressure treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a dressing for treating a tissue site with negative pressure may include a pressure indicator. The pressure indicator may include an enclosed space housing a non-woven wicking and manifolding layer and an encapsulated reticulated shape deforming foam member or another form of pressure deforming and/or deflecting material, such as a deformable polymer form, a hologram, a LCD, or any other suitable material. The dressing may reduce and/or prevent pressure or fluid communication with external environments other than at an end of the structure, which may be open and/or not covered or enclosed. The encapsulating material may be polyurethane (PU) or another thin, breathable material of about 15 microns to about 30 microns thick. In some embodiments, the foam encapsulation material may be formed such that there is no natural material compression of the materials that may cause compression while in storage prior to use. The materials of the pressure indicator may be soft, flexible, and breathable, such that the materials are unlikely to cause pressure points that may result in skin damage if placed near a wound. One end of the structure of the pressure indicator may be open and not enclosed so that the pressure indicator is in fluid communication with a tissue site. The end may fold under a portion of the dressing and face a tissue site so as to indicate a negative pressure delivered to tissues which may have been manifolded through an absorbent core of the dressing.

More generally, in some embodiments, a dressing for treating a tissue site with negative pressure may include a core comprising a first surface, a second surface, and an absorbent between the first surface and the second surface, a cover disposed over the first surface of the core, a pressure indicator configured to change shape under negative pressure, and a fluid conductor coupling the pressure indicator to the second surface of the core.

In some embodiments, a dressing for treating a tissue site with negative pressure may include a core comprising a first surface, a second surface comprising a first zone and a second zone, and an absorbent between the first surface and the second surface, a cover disposed over the first surface of the core, a first pressure indicator configured to change shape under negative pressure, a first fluid conductor coupling the first pressure indicator to the first zone, a second pressure indicator configured to change shape under negative pressure, and a second fluid conductor coupling the second pressure indicator to the second zone.

In some embodiments, a dressing for treating a tissue site with negative pressure may include a core comprising a first surface, a second surface, and an absorbent between the first surface and the second surface, a means for covering the first surface of the core, and a means for indicating a pressure change adjacent to the second surface of the core.

Alternatively, other example embodiments may include an apparatus for treating a tissue site with negative pressure. The apparatus may include a core comprising a first surface, a second surface, and an absorbent between the first surface and the second surface, a cover disposed over the first surface of the core, a pressure indicator configured to change shape under negative pressure, a fluid conductor coupling the pressure indicator to the second surface of the core, and a means for providing negative pressure to the core.

Objectives, advantages, and a preferred mode of making and using the claimed subject matter may be understood best

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
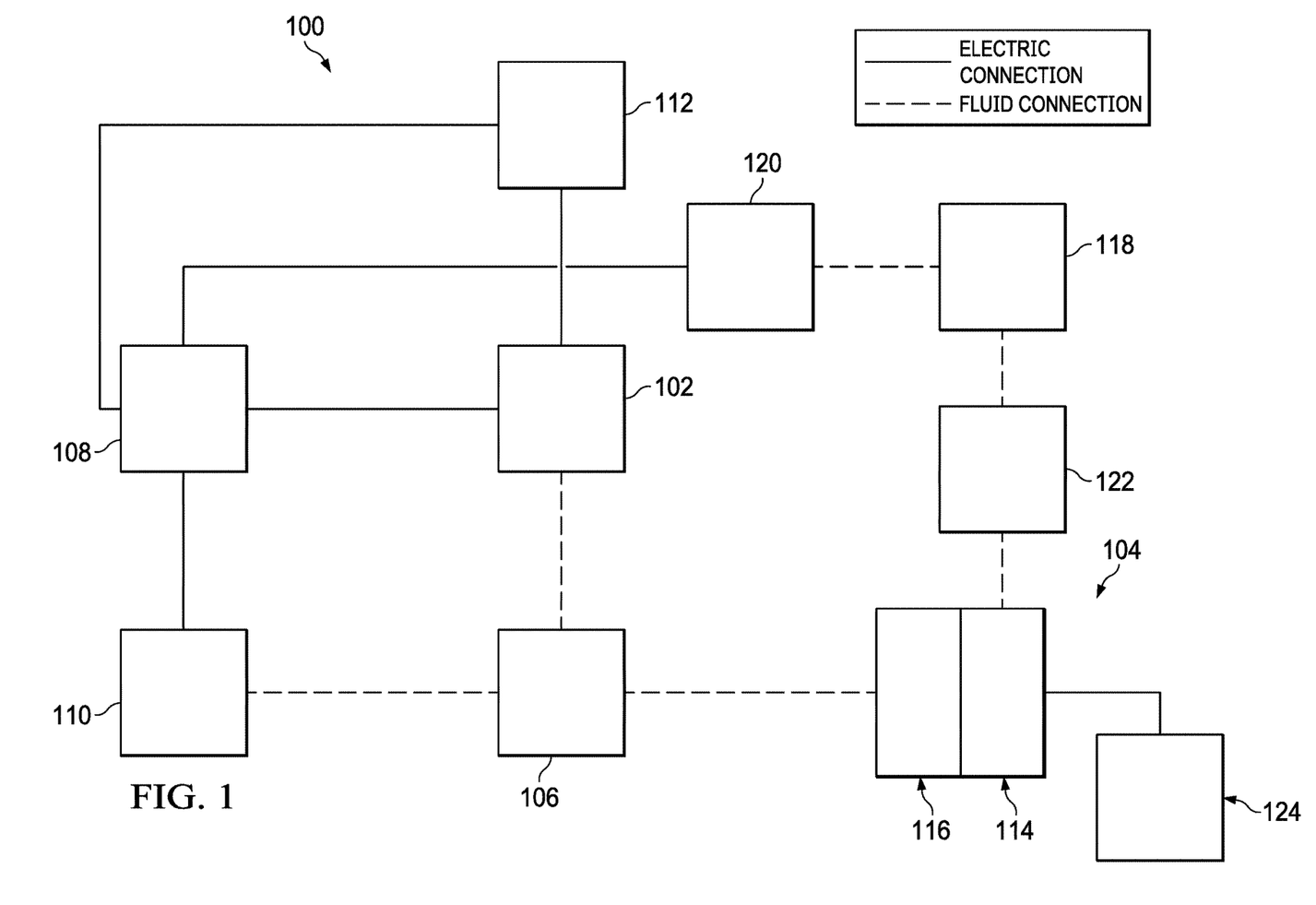
FIG. 1 is a functional block diagram of an example embodiment of a therapy system that can provide negative-pressure treatment with instillation in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 102, a dressing 104, a fluid container, such as a container 106, and a regulator or controller, such as a controller 108, for example. Additionally, the therapy system 100 may include sensors to measure operating parameters and provide feedback signals to the controller 108 indicative of the operating parameters. As illustrated in FIG. 1, for example, the therapy system 100 may include a pressure sensor 110, an electric sensor 112, or both, coupled to the controller 108. As illustrated in the example of FIG. 1, the dressing 104 may comprise or consist essentially of a tissue interface 114, a cover 116, or both in some embodiments, and a pressure indicator 124.

The therapy system 100 may also include a source of instillation solution. For example, a solution source 118 may be fluidly coupled to the dressing 104, as illustrated in the example embodiment of FIG. 1. The solution source 118 may be fluidly coupled to a positive-pressure source, such as the positive-pressure source 120, in some embodiments, or may be fluidly coupled to the negative-pressure source 102. A regulator, such as an installation regulator 122, may also be fluidly coupled to the solution source 118 and the dressing 104. In some embodiments, the instillation regulator 122 may also be fluidly coupled to the negative-pressure source 102 through the dressing 104, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the solution source 118, the controller 108 and other components into a therapy unit.

In general, components of the therapy system 100 may be coupled directly or indirectly. For example, the negative-pressure source 102 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. In some embodiments, components may also be coupled by virtue of physical proximity, being integral to a single structure, or being formed from the same piece of material. For example, the negative-pressure source 102 may be electrically coupled to the controller 108. The negative-pressure source 102 may be fluidly coupled to one or more distribution components, which provide a fluid path to a tissue site.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104. For example, such a dressing interface may be a SENSAT.R.A.C.™ Pad available from KCI of San Antonio, Tex.

A negative-pressure supply, such as the negative-pressure source 102, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the pressure sensor 110 or the electric sensor 112, are generally known in the art as any apparatus operable to detect or measure a physical phenomenon or property, and generally provide a signal indicative of the phenomenon or property that is detected or measured. For example, the pressure sensor 110 and the electric sensor 112 may be configured to measure one or more operating parameters of the therapy system 100. In some embodiments, the pressure sensor 110 may be a transducer configured to measure pressure in a pneumatic pathway and convert the measurement to a signal indicative of the pressure measured. In some embodiments, for example, the pressure sensor 110 may be a piezoresistive strain gauge. The electric sensor 112 may optionally measure operating parameters of the negative-pressure source 102, such as the voltage or current, in some embodiments. Preferably, the signals from the pressure sensor 110 and the electric sensor 112 are suitable as an input signal to the controller 108, but some signal conditioning may be appropriate in some embodiments. For example, the signal may need to be filtered or amplified before it can be processed by the controller 108. Typically, the signal is an electrical signal, but may be represented in other forms, such as an optical signal.

The tissue interface 114 can be generally adapted to contact a tissue site. The tissue interface 114 may be partially or fully in contact with the tissue site. If the tissue site is a wound, for example, the tissue interface 114 may partially or completely fill the wound, or may be placed over the wound. The tissue interface 114 may take many forms, and may have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites. Moreover, any or all of the surfaces of the tissue interface 114 may have projections or an uneven, course, or jagged profile that can induce strains and stresses on a tissue site, which can promote granulation at the tissue site.

In some embodiments, the tissue interface 114 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid such as from a source of instillation solution across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, open-cell foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 114 may be a foam having pore sizes in a range of 400-600 microns. The tensile strength of the tissue interface 114 may also vary according to needs of a prescribed therapy. For example, the tensile strength of a foam may be increased for instillation of topical treatment solutions. In one non-limiting example, the tissue interface 114 may be a reticulated polyurethane foam such as GRANUFOAM™ dressing or V.A.C. VERAFLO™ dressing, both available from KCI of San Antonio, Tex.

The tissue interface 114 may be either hydrophobic or hydrophilic. In an example in which the tissue interface 114 may be hydrophilic, the tissue interface 114 may also wick fluid away from a tissue site, while continuing to distribute negative pressure to the tissue site. The wicking properties of the tissue interface 114 may draw fluid away from a tissue site by capillary flow or other wicking mechanisms. An example of a hydrophilic foam is a polyvinyl alcohol, open-cell foam such as V.A.C. WHITEFOAM™ dressing available from KCI of San Antonio, Tex. Other hydrophilic foams may include those made from polyether. Other foams that may exhibit hydrophilic characteristics include hydrophobic foams that have been treated or coated to provide hydrophilicity.

The tissue interface 114 may further promote granulation at a tissue site when pressure within the sealed therapeutic environment is reduced. For example, any or all of the surfaces of the tissue interface 114 may have an uneven, coarse, or jagged profile that can induce microstrains and stresses at a tissue site if negative pressure is applied through the tissue interface 114.

In some embodiments, the tissue interface 114 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 114 may further serve as a scaffold for new cell-growth, or a scaffold material may be used in conjunction with the tissue interface 114 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may be, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 300 g/m^2 per twenty-four hours in some embodiments. In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

In general, the pressure indicator 124 may provide a means for indicating pressure changes, and may be fluidly coupled to a side of the tissue interface 114 opposite the cover 116. In some embodiments, the pressure indicator 124 may include a force collector, and a fluid conductor or fluid bridge that fluidly couples the force collector to the side of the tissue interface 114 opposite the cover 116. A force collector may comprise, for example, a pneumatic spring or diaphragm configured to be deflected by an increase in negative pressure. In some embodiments, a force collector may comprise compressible or elastic foam substantially encapsulated in a compliant, fluid-impermeable housing, such as polyurethane film. In other embodiments, a force collector may comprise a resilient molded polymer. Other examples of suitable indicators may include holograms or liquid-crystal displays.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 116 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

Figure 2:
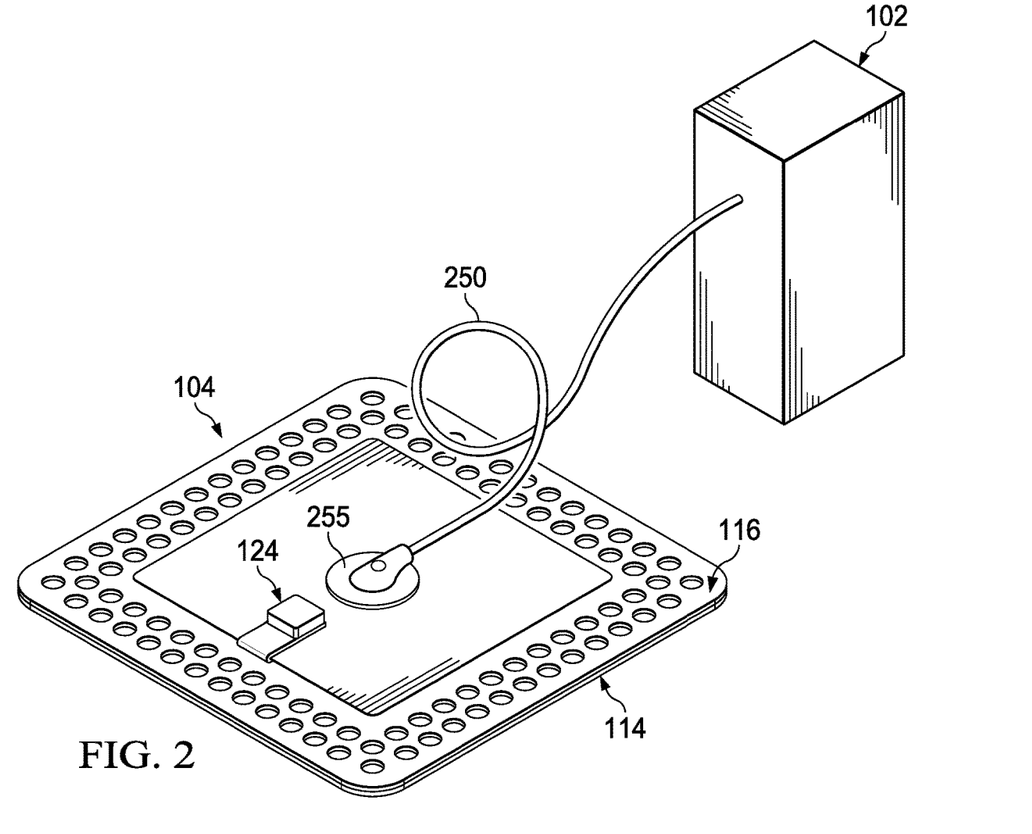
FIG. 2 is a schematic view of an example of the therapy system of FIG. 1.

FIG. 2 is a schematic view of an example of the therapy system of FIG. 1, illustrating additional details that may be associated with some embodiments. The negative-pressure source 102 may be a portable vacuum pump, for example, which can be manually-actuated or powered by batteries in some embodiments. In the example embodiment of FIG. 2, the dressing 104 generally includes the pressure indicator 124, the tissue interface 114, and the cover 116.

In some embodiments, as shown in FIG. 2, the therapy system may include one or more fluid conductors, such as tubing 250, and a dressing interface 255. As shown in the example of FIG. 2, the tubing 250 may include flexible tube, which can be fluidly coupled on one end to the dressing interface 255. In some embodiments, the dressing interface 255 may be an elbow connector, as shown in the example of FIG. 2. The negative-pressure source 102 may be in fluid communication with the dressing interface 255 via the tubing 250. In the example of FIG. 2, at least a portion of the pressure indicator 124 may be visible through the cover 116.

Figure 3:
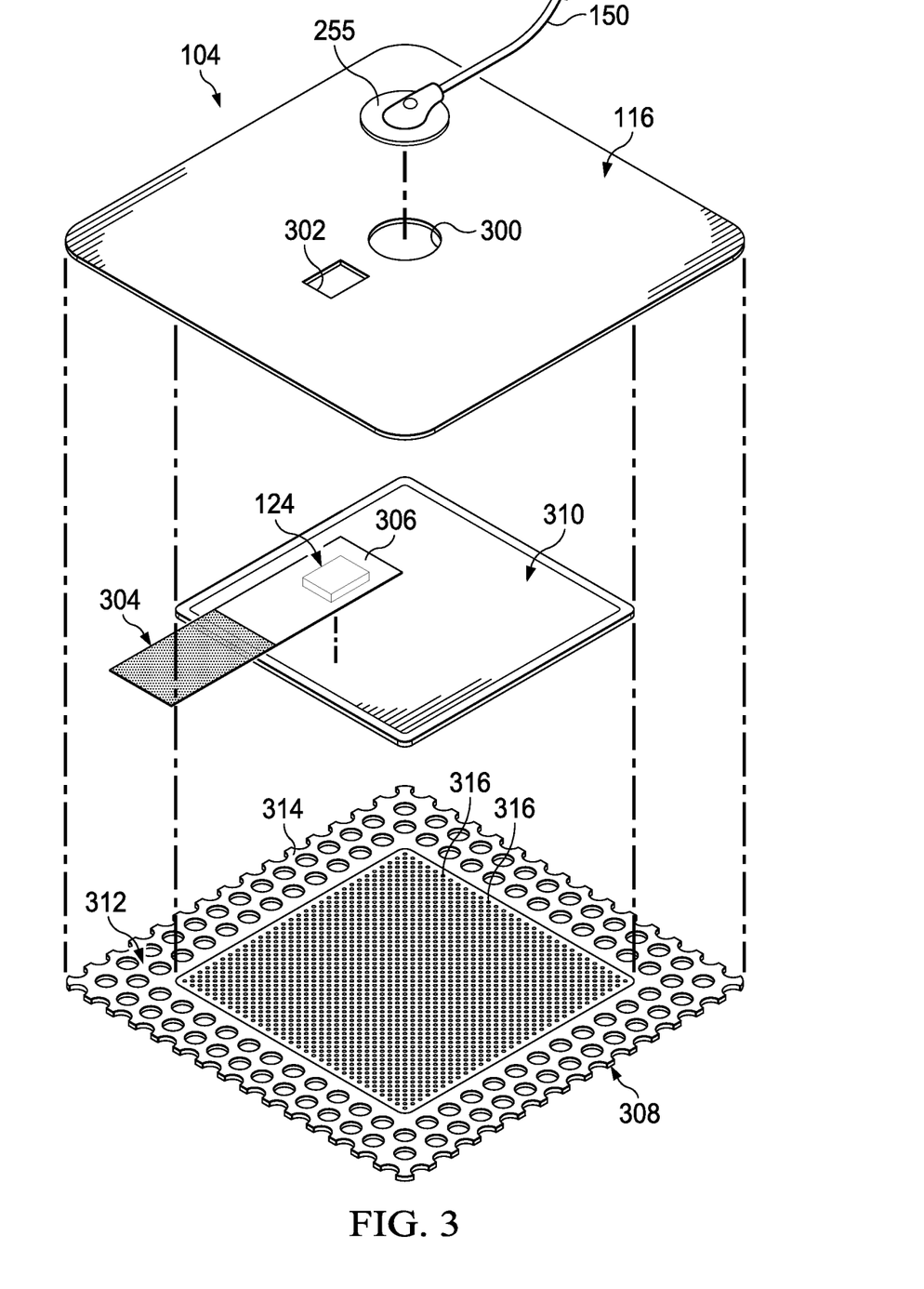
FIG. 3 is an exploded view of the dressing of FIG. 2.

FIG. 3 is an exploded view of the dressing 104 of FIG. 2, illustrating additional details that may be associated with some embodiments. In some embodiments, as shown in FIG. 3, the cover 116 may include a first aperture 300 and a second aperture 302. The dressing interface 255 can be placed over the first aperture 300 in the cover 116 to provide a fluid path between the tubing 250 and the dressing interface 255.

In the example of FIG. 3, the pressure indicator 124 may extend through and/or be visible through the second aperture 302 when assembled. For example, in some embodiments the pressure indicator 124 may protrude through the second aperture to minimize or eliminate external compression on the pressure indicator 124. In some embodiments, the pressure indicator 124 may also include a sealing flange 306. The sealing flange 306 may substantially surround the pressure indicator 124 in some embodiments. At least a portion of the sealing flange 306 may lay between the cover 116 and the tissue interface 114 when the dressing 104 is assembled. A fluid conductor 304 can form a fluid path from and may be in fluid communication with the pressure indicator 124. In some embodiments, for example, the fluid conductor may comprise or consist essentially of a non-woven wicking and manifold material. Examples of materials that may be suitable for some embodiments of the fluid conductor 304 include Libeltex TDL2 80 gsm, 3D textiles, stitched textiles, foam, and porous polymers.

In some embodiments, the tissue interface 114 may comprise or consist of an absorbent layer or core. In other embodiments, the tissue interface 114 may comprise more than one layer or functional component. In the example of FIG. 3, the tissue interface 114 includes an interface layer 308 and a fluid management core 310. Assembled, the interface layer 308 may be coupled to a periphery of the cover 116 so as to enclose the fluid management core 310 between the interface layer 308 and the cover 116.

The interface layer 308 may comprise or consist essentially of a sealing layer formed from a soft, pliable material suitable for providing a fluid seal with a tissue site, and may have a substantially flat surface. For example, the interface layer 308 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. In some embodiments, the interface layer 308 may have a thickness between about 200 microns (μm) and about 1000 microns (μm). In some embodiments, the interface layer 308 may have a hardness between about 5 Shore OO and about 80 Shore OO. Further, the interface layer 308 may be comprised of hydrophobic or hydrophilic materials.

The interface layer 308 may have a periphery 312 surrounding or around an interior portion 314, and may have apertures 316 disposed through the periphery 312 and the interior portion 314 configured to transfer fluid through the interface layer 308. The interface layer 308 may have an interior border around the interior portion 314, disposed between the interior portion 314 and the periphery 312. The interior border may be substantially free of the apertures 316 in some embodiments. In some examples, as illustrated in FIG. 3, the interior portion 314 may be symmetrical and centrally disposed in the interface layer 308.

Figure 4:
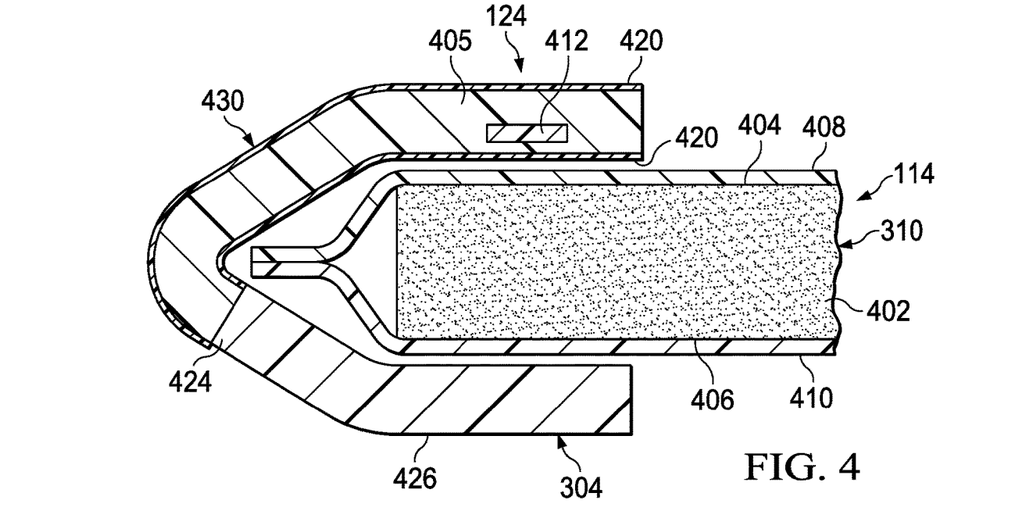
FIG. 4 is a partial cross-sectional view of a dressing including a pressure indicator that may be associated with some embodiments of the therapy system of FIG. 1.

FIG. 4 is a partial cross-sectional view of examples of the fluid management core 310 and the pressure indicator 124, illustrating additional details that may be associated with some embodiments. In some embodiments, as shown in FIG. 4, the fluid management core 310 may include an absorbent 402 having a first surface 404 and a second surface 406. The absorbent 402 may be foam or other manifold material, and may be a superabsorbent material. In some embodiments, the fluid management core 310 may also include a first wicking layer 408 and/or a second wicking layer 410. The first wicking layer 408 and the second wicking layer 410 may surround or envelope the absorbent 402 in some embodiments.

In some embodiments, the pressure indicator 124 may be supported at least in part by the first surface 404 of the absorbent 402 or by the first wicking layer 408. In the example of FIG. 4, the pressure indicator 124 comprises a force collector 430, which may comprise a manifold 405 that is at least partially enclosed by a film 420. The manifold 405 may comprise or consist of an elastic material, and can function as a pneumatic spring. The film 420 may be a polymer film, such as polyurethane or any other thin, breathable material having a thickness ranging from about 15 microns to about 30 microns (e.g., about 20 microns to about 25 microns). The film 420 may be vacuum-formed to minimize or eliminate natural compression on the manifold 405.

As illustrated in the example of FIG. 4, the pressure indicator 124 may also include a token, icon, marker, or other type of an indicator marker 412. In FIG. 4, the indicator marker 412 is positioned under the manifold 405. The indicator marker 412 may be formed of a low-profile, soft and/or semi-rigid polymer, for example. In some embodiments, the manifold 405 may be low-density foam that allows the indicator marker 412 to be seen when the manifold 405 is compressed. In some embodiments, the manifold 405 may have a thickness of about 3 mm to about 4 mm when uncompressed, and a thickness of about 1 mm when compressed. Because at least a portion of the pressure indicator 124 is encapsulated, fluid communication with external environments other than at the fluid conductor 304 can be reduced or minimized.

In some embodiments, the pressure indicator 124 also includes an open portion, which may include the fluid conductor 304. In some embodiments, the fluid conductor 304 may be an extension of the manifold 405. The fluid conductor 304 of FIG. 4 includes a first end 424 that is in fluid communication with the manifold 405, and a second end 426 that is positioned adjacent to the second surface 406 or adjacent to the second wicking layer 410. The fluid conductor 304 may be formed of a same material as the manifold 405, or the fluid conductor 304 may be formed of a different material than the manifold 405. The fluid conductor 304 is not encapsulated so that the fluid conductor 304 is exposed to the same pressure that the tissue interface 114 and underlying tissues are exposed to during therapy. The fluid conductor 304 can form a fluid path around the fluid management core 310, as illustrated in the example of FIG. 4, or may provide an isolated fluid path through the fluid management core 310 in some embodiments. The force collector 430 may only be in fluid communication with the fluid conductor 304, such that pressure from other external environments is not communicated to the force collector 430.

Figure 5:
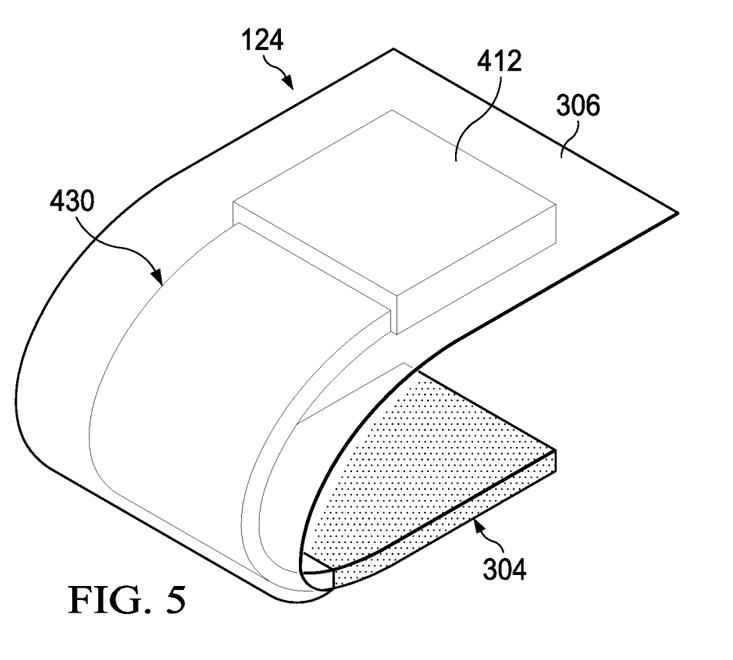
FIG. 5 is a perspective view of a dressing including a pressure indicator that may be associated with some embodiments of the therapy system of FIG. 1.

FIG. 5 is a perspective view of another example of the pressure indicator 124, illustrating additional details that may be associated with some embodiments. In some embodiments, the indicator marker 412 may be substantially square or rectangular in shape. The indicator marker 412 may be a polymer form embedded within a foam material. In some embodiments, the indicator marker 412 is a marking or token that can become visible if the foam is compressed. The indicator marker 412 may be encapsulated within the film 420, which can also form the sealing flange 306 in some embodiments. The film 420 may provide a pre-tensioned seal over the pressure indicator 124 in some embodiments. The sealing flange 306 can provide a surface that may be used to adhere or connect the pressure indicator 124 to a top surface of the fluid management core 310 and/or a bottom surface of the cover 116.

Figure 6:
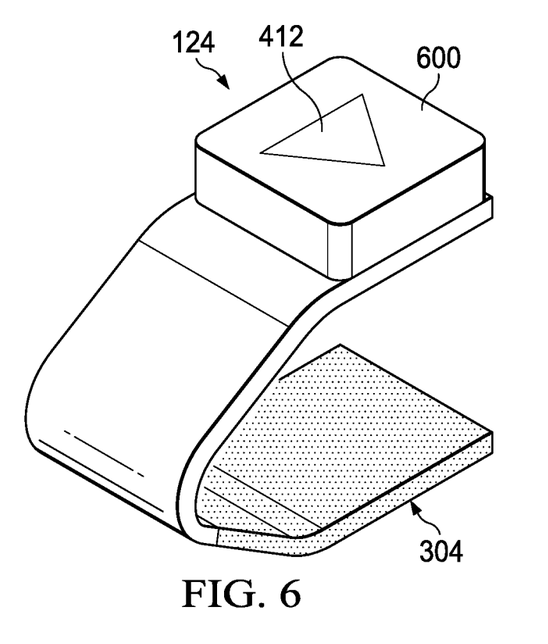
FIG. 6 is a perspective view of an example of a pressure indicator that may be associated with some embodiments of the therapy system of FIG. 1.

FIG. 6 is a perspective view of another example of the pressure indicator 124, illustrating additional details that may be associated with some embodiments. In some embodiments, the pressure indicator 124 includes the indicator marker 412 embedded in an encapsulated foam section 600. The indicator marker 412 may be formed of a low-profile, soft and/or semi-rigid polymer. If negative pressure is communicated to the encapsulated foam section 600 through the fluid conductor 304, the encapsulated foam section 600 may be compressed so that the indicator marker 412 becomes visible through the encapsulated foam section 600. The indicator marker 412 may be shaped as a triangle, circle, square, rectangle, hexagon, octagon, or any other shape.

Figure 7:
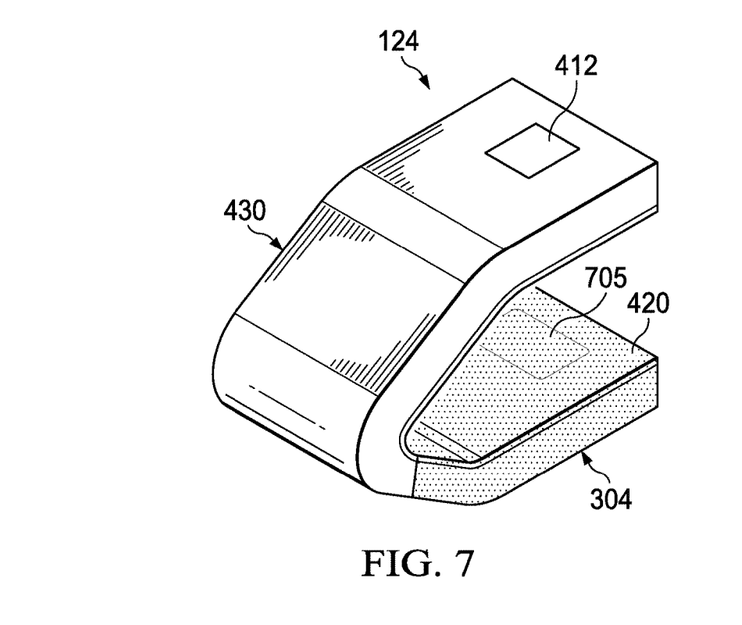
FIG. 7 is a perspective view of an example of a pressure indicator that may be associated with some embodiments of the therapy system of FIG. 1.

FIG. 7 is a perspective view of another example of the pressure indicator 124, illustrating additional details that may be associated with some embodiments. In some embodiments, the pressure indicator 124 includes the force collector 430 along a length thereof. The indicator marker 412 can be inserted or embedded in a first end of the force collector 430, and the fluid conductor 304 can be inserted or embedded in a second end of the force collector 430. As illustrated in the example of FIG. 7, some embodiments of the fluid conductor 304 may comprise a manifold 705 at least partially enclosed by the film 420, and the film 420 may have an open end exposing the manifold 705. The fluid conductor 304 can be arranged such that the fluid conductor 304 extends through a thickness of the force collector 430 and the fluid conductor 304 contacts the tissue interface 114. The pressure indicator 124 can be arranged so that the indicator body 412 becomes visible through the second aperture 302 of the cover 116 of the dressing 104.

Figure 8:
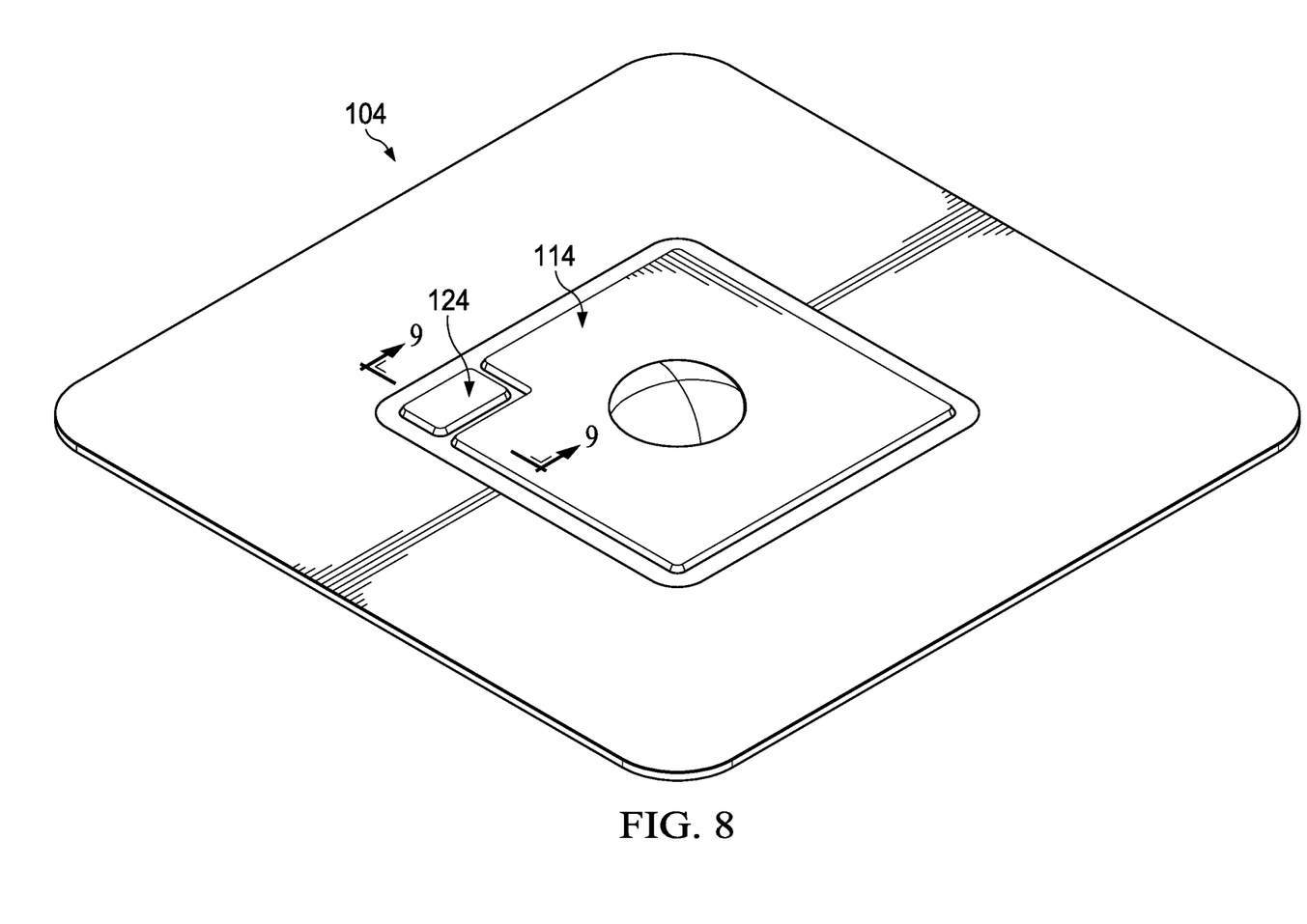
FIG. 8 is a perspective view of another example of a dressing that may be associated with some embodiments of the therapy system of FIG. 1.

FIG. 8 is a perspective view of another example of the dressing 104, illustrating additional details that may be associated with some embodiments. As illustrated in the example of FIG. 8, the pressure indicator 124 may be integrated with the tissue interface 114 of the dressing 104 in some embodiments.

Figure 9:
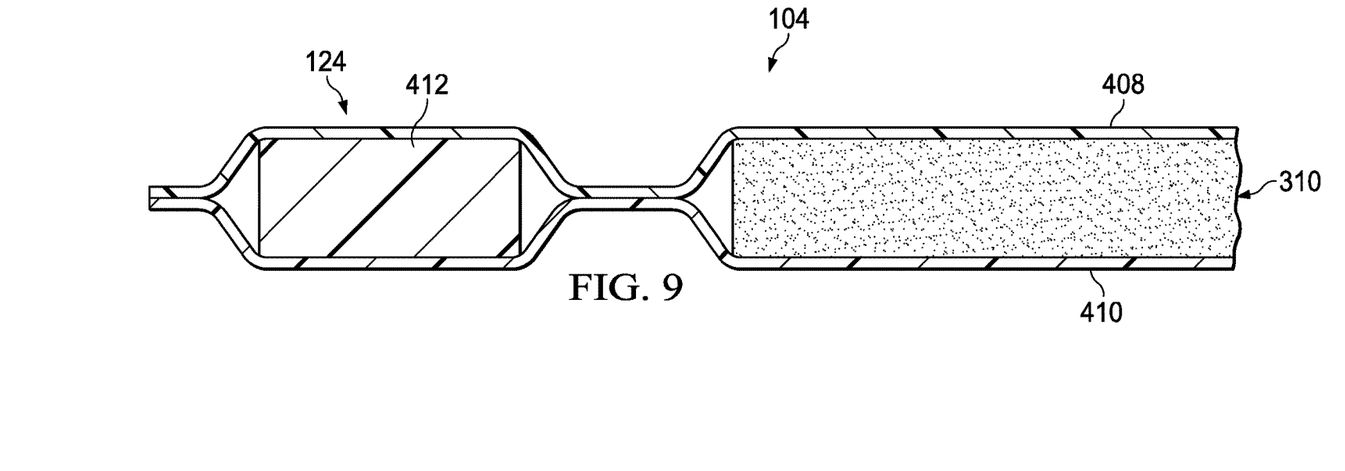
FIG. 9 is a partial cross-sectional view of the dressing of FIG. 8.

FIG. 9 is a cross-sectional view of the dressing 104 of FIG. 8. In some embodiments, the pressure indicator 124 includes the indicator marker 412, which may be formed of compressible foam, for example. The pressure indicator 124 can be disposed adjacent to or coupled to the fluid management core 310. The first wicking layer 408 and the second wicking layer 410 can also cover the indicator marker 412 in some embodiments. In general, the bottom surface of the pressure indicator 124 is in the same plane as the bottom surface of the fluid management core 310. When applied to tissues, pressure delivered to the tissue interface 114 is also communicated to the pressure indicator 124.

Figure 10:
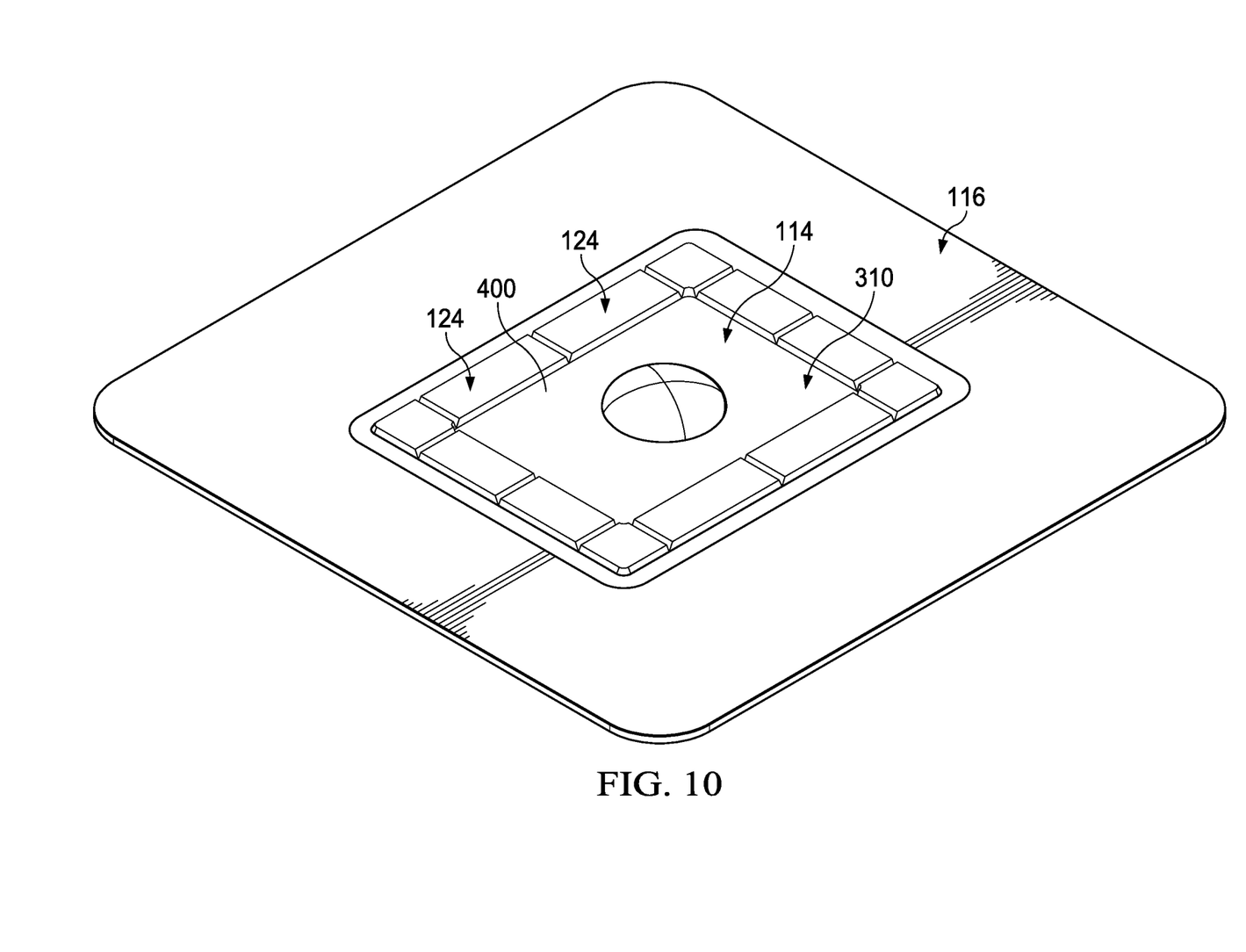
FIG. 10 is a perspective view of another example of a dressing that may be associated with some embodiments of the therapy system of FIG. 1.

FIG. 10 is a perspective view of another example of the dressing 104, illustrating additional details that may be associated with some embodiments of the therapy system of FIG. 1. In some embodiments, the dressing 104 may include multiple pressure indicators 124. The pressure indicators 124 may be integrally formed with the fluid management core 310 in some examples. The dressing 104 may include between one and twenty zones. Each zone may include one of the pressure indicators 124. The dressing 104 may include multiple pressure indicators 124 along each side of the fluid management core 310. Each of the pressure indicators 124 may be a same size or a different size as other pressure indicators 124. Use of multiple pressure indicators 124 may provide an indication of delivery of negative-pressure therapy along an entirety of the fluid management core 310.

Figure 11:
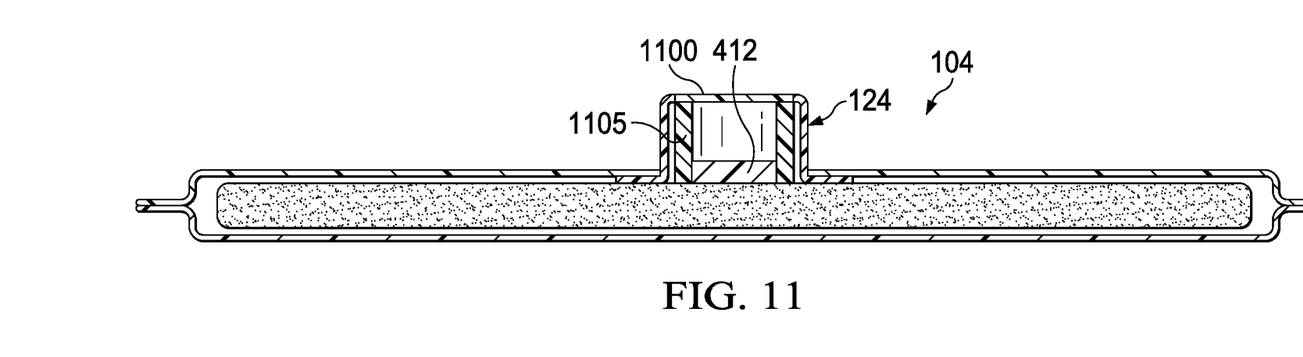
FIG. 11 is a schematic view of another dressing that may be associated with some embodiments of the therapy system of FIG. 1, illustrating a first state of an example of a pressure indicator when negative pressure is not applied.

FIG. 11 is a schematic view of another example of the dressing 104, illustrating additional details that may be associated with some embodiments. For example, FIG. 11 illustrates another embodiment of the pressure indicator 124 in a state when negative pressure is not applied. In some embodiments, the pressure indicator 124 may include a polarizing film 1100, which may obscure the indicator marker 412 before negative pressure is applied. In this embodiment, a mount 1105 may include a compressible and/or opaque material, such as foam, which forms a compressible mount. The polarized film 1100 may be mounted on the manifold 405. The polarized film 1100 can be configured to substantially prevent light from escaping the pressure indicator 124. For example, in the state illustrated in FIG. 11, the mount 1105 supports the polarized film 1100 and separates the polarized film 1100 from the indicator marker 412, which can obscure the indicator marker 412.

Figure 12:
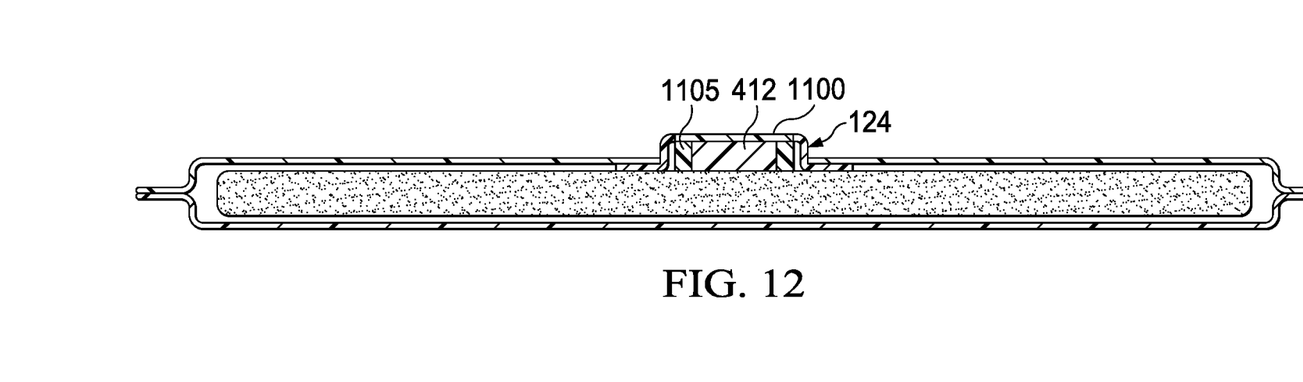
FIG. 12 is a schematic view of the dressing of FIG. 11, illustrating a second state of the pressure indicator when negative pressure is applied.

FIG. 12 is a cross-sectional view of the dressing 104 of FIG. 11, illustrating additional details that may be associated with the pressure indicator 124 in a state when negative pressure is applied to an underside of the dressing 104. In some embodiments, as the mount 1105 collapses due to application of negative pressure, the polarized film 1100 can be moved adjacent to the indicator marker 412, and a light-colored surface of the indicator marker 412 can become visible to indicate application of negative pressure to the underside of the dressing 104. In lieu of a light-colored surface, the indicator marker 412 may include text, a marker, or an icon that indicates that negative pressure is being applied to an underside of the dressing 104.

In some embodiments, the indicator marker 412 may be a color that is different than a color of the mount 1105. In other embodiments, the indicator marker 412 may be formed in different shapes and/or may include indicia printed thereon. When negative therapy pressure is applied at the fluid conductor 304 and underside of the dressing 104, the shaped and/or the indicia on the indicator marker 412 becomes visible.

In operation, the tissue interface 114 may be placed within, over, on, or otherwise proximate to a tissue site. The cover 116 may be placed over the tissue interface 114 and sealed to an attachment surface near the tissue site. For example, the cover 116 may be sealed to undamaged epidermis peripheral to a tissue site. Thus, the dressing 104 can provide a sealed therapeutic environment proximate to a tissue site, substantially isolated from the external environment, and the negative-pressure source 102 can reduce the pressure in the sealed therapeutic environment. Negative pressure applied across the tissue site through the tissue interface 114 in the sealed therapeutic environment can induce macrostrain and micro-strain in the tissue site, as well as remove exudates and other fluids from the tissue site, which can be collected in container 106.

The therapy system 100 can also provide a visual indication that pressure is being delivered to a tissue site. For example, the pressure indicator 124 can provide a fluid path around or through the tissue interface 114 so that the indicator marker 412 is subjected to the same pressure change as the side of the tissue interface 114 adjacent to a tissue site. If negative pressure is applied to the side of the tissue interface 114 facing a tissue site, the pressure indicator 124 can be compressed, deflected, or otherwise change shape to provide a visual indication of pressure change. Additionally or alternatively, the indicator marker 412 can become visible through or within the pressure indicator 124. For example, the pressure indicator 124 may be configured to have a first shape at atmospheric pressure and a second shape under negative pressure. The first shape may obscure the indicator marker 412, and the second shape may reveal the indicator marker 412.

In some embodiments of the therapy system 100, the pressure indicator 124 may indicate an impediment to pressure delivery, such as saturation of the dressing 104.

The systems, apparatuses, and methods described herein may provide significant advantages. For example, use of the pressure indicator 124 with an absorbent in the dressing 104 may indicate when the dressing 104 is saturated or otherwise preventing application of negative pressure to an underside of the dressing 104. The use of soft, breathable, and/or flexible materials to form the pressure indicator 124 can substantially reduce or eliminate skin damage and/or pressure points during therapy. The pressure indicator 124 can be used with a variety of embodiments of the dressing 104, and may be particularly advantageous with an absorbent dressing. The cover 116 can be manufactured or retrofitted with apertures to fit the pressure indicator 124 with the dressing 104.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 104, the pressure indicator 124, or both may be separated from other components for manufacture or sale.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site with negative pressure, the dressing comprising:
   a core comprising a first surface, a second surface, and an absorbent between the first surface and the second surface;
   a cover disposed over the first surface of the core;
   a pressure indicator configured to change shape under negative pressure; and
   a fluid conductor comprising a fluid path around the core for coupling the pressure indicator to the second surface of the core.

2. The dressing of claim 1, wherein the pressure indicator comprises compressible foam.

3. The dressing of claim 1, wherein the pressure indicator comprises compressible foam and a pre-tensioned seal over the compressible foam.

4. The dressing of claim 1, wherein the pressure indicator comprises a deformable polymer form.

5. The dressing of claim 1, wherein:
   the cover comprises an aperture; and
   the pressure indicator is supported by the first surface and protrudes through the aperture.

6. The dressing of claim 1, wherein:
   the cover comprises an aperture;
   the pressure indicator is supported by the first surface and protrudes through the aperture;
   the pressure indicator comprises a sealing flange around the aperture; and
   the fluid conductor comprises an isolated fluid path through the core.

7. The dressing of claim 1, further comprising:
   an aperture in the cover; and
   a dressing interface fluidly coupled to the core through the aperture.

8. The dressing of claim 1, wherein the fluid conductor comprises a manifold at least partially enclosed by a fluid-impermeable film having an open end fluidly coupled to the second surface.

9. The dressing of claim 1, wherein the core further comprises a first wicking layer and a second wicking layer adjacent to opposing sides of the absorbent.

10. The dressing of claim 1, further comprising an interface layer coupled to a periphery of the cover to enclose the core between the interface layer and the cover.

11. The dressing of claim 10, wherein the interface layer comprises:
    an adhesive that is substantially impermeable to fluid; and
    a plurality of apertures configured to transfer fluid through the interface layer.

12. The dressing of claim 11, wherein the adhesive is silicone.

13. The dressing of claim 1, wherein:
    the pressure indicator comprises a marker;
    the pressure indicator is configured to have a first shape at atmospheric pressure and a second shape at negative pressure;
    the first shape obscures the marker; and
    the second shape reveals the marker.

14. The dressing of claim 13, wherein the marker comprises at least one of a color, text, shape, and image.

15. The dressing of claim 1, wherein:
    the pressure indicator comprises a marker and a polarized film; and
    the polarized film is configured to obscure the marker at atmospheric pressure and to reveal the marker at negative pressure.

16. The dressing of claim 15, wherein:
    the pressure indicator further comprises a compressible mount; and the polarized film is coupled to the compressible mount over the marker.

17. An apparatus for treating a tissue site with negative pressure, the apparatus comprising:
  a core comprising a first surface, a second surface, and an absorbent between the first surface and the second surface;
  a cover disposed over the first surface of the core;
  a pressure indicator configured to change shape under negative pressure;
  a fluid conductor comprising a fluid path around the core for coupling the pressure indicator to the second surface of the core; and
  a means for providing negative pressure to the core.

18. The apparatus of claim 17, wherein the means for providing negative pressure is one of a vacuum pump, a suction pump, a wall suction port, or a micro-pump.

19. A dressing for treating a tissue site with negative pressure, the dressing comprising:
  a core comprising a first surface, a second surface, and an absorbent between the first surface and the second surface;
  a cover disposed over the first surface of the core;
  a pressure indicator configured to change shape under negative pressure; and
  a fluid conductor coupling the pressure indicator to the second surface of the core, wherein the fluid conductor comprises a manifold at least partially enclosed by a fluid-impermeable film having an open end fluidly coupled to the second surface.

20. A dressing for treating a tissue site with negative pressure, the dressing comprising:
  a core comprising a first surface, a second surface, and an absorbent between the first surface and the second surface;
  a cover disposed over the first surface of the core;
  a pressure indicator configured to change shape under negative pressure and comprising a marker, a polarized film, and a compressible mount, the polarized film coupled to the compressible mount over the marker and being configured to obscure the marker at atmospheric pressure and to reveal the marker at negative pressure; and
  a fluid conductor coupling the pressure indicator to the second surface of the core.

\* \* \* \* \*